US008961894B2

(12) United States Patent
Keener et al.

(10) Patent No.: US 8,961,894 B2
(45) Date of Patent: Feb. 24, 2015

(54) GENERATION OF MICROBIOCIDE INSIDE A PACKAGE UTILIZING A CONTROLLED GAS COMPOSITION

(75) Inventors: Kevin M. Keener, Attica, IN (US); Jeanette L. Jensen, Oxford, IN (US)

(73) Assignee: Purdue Research Foundation, West Lafayette, IN (US)

( * ) Notice: Subject to any disclaimer, the term of this patent is extended or adjusted under 35 U.S.C. 154(b) by 0 days.

(21) Appl. No.: 14/004,030

(22) PCT Filed: Mar. 9, 2012

(86) PCT No.: PCT/US2012/028413
§ 371 (c)(1),
(2), (4) Date: Oct. 15, 2013

(87) PCT Pub. No.: WO2012/125435
PCT Pub. Date: Sep. 20, 2012

(65) Prior Publication Data
US 2014/0044595 A1    Feb. 13, 2014

Related U.S. Application Data

(63) Continuation-in-part of application No. 12/861,106, filed on Aug. 23, 2010, which is a continuation-in-part of application No. 12/726,097, filed on Mar. 17, 2010, now abandoned.

(Continued)

(51) Int. Cl.
*A61L 9/00* (2006.01)
*H05F 3/00* (2006.01)
(Continued)

(52) U.S. Cl.
CPC ............. *A61L 2/14* (2013.01); *H01J 37/32348* (2013.01); *H01J 37/32825* (2013.01)

USPC ............ 422/305; 422/306; 204/164; 250/326

(58) Field of Classification Search
CPC .............. A61L 2/00; A61L 9/22; A61L 12/00
USPC .............. 422/1, 4, 22, 121, 186.04, 305–306; 204/157.15, 164; 205/147; 250/326
See application file for complete search history.

(56) References Cited

U.S. PATENT DOCUMENTS

| 4,524,080 | A | 6/1985 | Sugisawa et al. |
| 5,302,343 | A | 4/1994 | Jacob |

(Continued)

FOREIGN PATENT DOCUMENTS

| DK | WO 2009/040130 A1 * | 4/2009 | ............. A61L 12/14 |
| WO | WO 2009/040130 A1 | 4/2009 | |

OTHER PUBLICATIONS

PCT International Search Report and Written Opinion for related PCT application No. PCT/US2012/028413.

(Continued)

*Primary Examiner* — Monzer R Chorbaji
(74) *Attorney, Agent, or Firm* — Brinks Gilson & Lione

(57) ABSTRACT

An apparatus and method of producing an atmospheric non-equilibrium plasma (ANEP) in a sealed container having a selected working gas and an object to be treated is described. A variety of working gas mixtures including air, $O_2$, $N_2$, $CO_2$, He and Ar, in combination with a range of ionization gradients, voltages and ANEP column lengths was investigated so as to establish effective ranges of the variables using the sterilization of a sample as a measure of effectiveness. Certain combinations of working gas, voltage gradient, voltage and ANEP column length were found to have greater effectiveness. The approach may be used for food products, medical equipment, or other objects where treatment with reactive gas atmospheres is effective.

25 Claims, 6 Drawing Sheets

Related U.S. Application Data

(60) Provisional application No. 61/162,785, filed on Mar. 24, 2009, provisional application No. 61/306,774, filed on Feb. 22, 2010, provisional application No. 61/451,975, filed on Mar. 11, 2011.

(51) Int. Cl.
*H01T 19/04* (2006.01)
*A61L 2/14* (2006.01)
*H01J 37/32* (2006.01)

(56) References Cited

U.S. PATENT DOCUMENTS

| | | | |
|---|---|---|---|
| 5,770,739 | A | 6/1998 | Lin |
| 6,228,330 | B1 | 5/2001 | Herrmann |
| 8,372,460 | B2 | 2/2013 | Meyers et al. |
| 2002/0136679 | A1 | 9/2002 | Frieze et al. |
| 2008/0106206 | A1 | 5/2008 | Hooke et al. |
| 2008/0260578 | A1 | 10/2008 | Engemann |
| 2009/0010818 | A1 | 1/2009 | Song |
| 2011/0014330 | A1 | 1/2011 | Meyers et al. |
| 2011/0268850 | A1 | 11/2011 | Rasanayagam et al. |
| 2012/0156341 | A1 | 6/2012 | Rasanayagam et al. |

OTHER PUBLICATIONS

Kevin M. Keener, "Quality and Safety Assessment of Packaged Spinach Treated with a Novel Atmospheric, Non-Equilibrium Plasma System", Paper No. 084396, presented at 2008 ASABE Annual Interational Meeting, Jun. 29-Jul. 2, 2008.

K.G. Kostov, R.Y. Honda, L.M.S. Alves, M.E. Kayama; "Characteristics of Dielectric Barrier Discharge Reactor for Material Treatment", Brazilian Journal of Physics, vol. 39, No. 2, Jun. 2009, pp. 322-325, IEEE Log No. 9412958.

Jing Li, Wanming Sun, Bijan Pashaie, Shirshak K. Dhali; "Streamer Discharge Simulation in Flue Gas", IEE Transactions on Plasma Science, vol. 23, No. 4, Aug. 1995, pp. 672-678.

F.J. Critzer et al., "Atmospheric Plasma Inactivation of Foodborne Pathogens on Fresh Produce Surfaces", J. Food Prot. Oct. 2007 pp. 2290-2296.

M. Laroussi et al., "Evaluation of the Roses of Reactive Species, Heat, and UV Radiation in the Inactivation of Bacterial Cells by Air Plasmas at Atmospheric Pressure", International Journal of Mass Spectrometry, vol. 223, Issues 1 and 3, Apr. 15, 2004; pp. 81-86.

\* cited by examiner

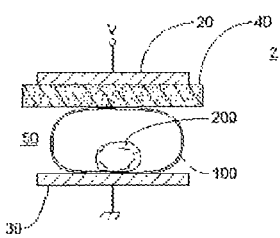
FIG. 2A
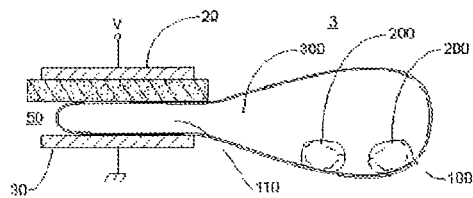
FIG. 2B
FIG. 2C

GENERATION OF MICROBIOCIDE INSIDE A PACKAGE UTILIZING A CONTROLLED GAS COMPOSITION

The present application claims priority to U.S. provisional application No. 61/451,975, filed on Mar. 11, 2011, which is incorporated herein by reference, and is a continuation in part of U.S. application Ser. No. 12/861,106, filed on Aug. 23, 2010, which is incorporated herein by reference and which is a continuation in part of U.S. application Ser. No. 12/726,097, (now abandoned), filed on Mar. 17, 2010 which claims priority to U.S. provisional application No. 61/306,774, filed on Feb. 22, 2010, and U.S. provisional application No. 61/162,785, filed on Mar. 24, 2009, each of which is incorporated herein by reference.

TECHNICAL FIELD

The present application relates an apparatus and method for treating packaged products to reduce undesirable contamination from viruses, bacteria, yeast, and mold, including spores and toxins, or for other treatment using a reactive gas atmosphere.

BACKGROUND

Biological decontamination and surface sterilization is crucial throughout society: in military applications such as the decontamination of equipment and facilities exposed to deadly biological agents, or in a broad array of civilian applications including medical applications, food production and consumer goods. Chemical, heat, high-energy electron beams, x-ray or gamma-ray irradiation systems are presently used in commercial treatments; however, utilization of these systems may not be practical due to the cost, efficiency, immobility, electric power requirements, toxic waste, personal hazard and the time required to decontaminate items.

Over the last decade, considerable research has been conducted in using atmospheric plasmas as a decontamination method of surfaces. Atmospheric plasmas have the ability to generate unique radiolytic profiles. Research has shown that biological contaminants exposed to atmospheric plasmas can be sterilized in seconds to minutes. Atmospheric plasmas are fairly easy to produce; and, the equipment needed is relatively inexpensive. There are no hazardous wastes and the gaseous by-products can be locally controlled. Up to this time, utilization of atmospheric plasmas has been through sealed chambers and jets.

Atmospheric, non-equilibrium plasma (ANEP) is an example of a non-thermal processing method. There is a wide variance in the terminology for the process to produce such a plasma. In the literature, a variety of terminology is used to describe the phenomenon including atmospheric glow discharge, surface barrier discharge (SBD), dielectric barrier discharge (DBD), Single Dielectric Barrier Discharge (SDBD) and Surface Plasma Chemistry Process (SPCP). For convenience herein, the term dielectric barrier discharge (DBD) is used, without intending to exclude any of the ANEP plasma generating mechanisms implied by choosing a specific terminology for description of the technique herein.

FIG. 1 shows simplified examples of DBD configurations that may be used to produce an ANEP in an ambient air environment. A high voltage generator 10 applies an alternating current potential to a pair of metallic plates 20, 30, spaced apart from each other to form a region 50 in which an object may be placed. At least one dielectric layer 40 is disposed between a first plate 20 and the second plate 30. In this manner, the effect of the dielectric layer is to limit the current of any filamentary discharge that is formed between the plate 20, 30 so as to prevent the formation of a high current arc. The discharge in region 50 is thus limited in energy and results in an ANEP where variety of reactive species may be formed from the gas (He, $O_2$, $N_2$, $CO_2$ and water vapor) and/or interaction with the packaged product. FIG. 1A shows a configuration with one dielectric layer 40 laid against an electrode 20. FIG. 1B shows an example where a dielectric plate 40 is laid against an electrode 20 and another dielectric plate 60 is laid against a second electrode 30. The charge accumulation on the plates which may be used in conjunction with the voltage waveform to estimate the power consumption may be measured by determining the voltage developed across a conventional capacitor 75. FIG. 1C illustrates a situation where a single dielectric layer 50 is disposed between the electrodes 20, 30, so that there are two regions 50 in which an ANEP may be produced.

As the possibility of an arc forming directly between the plates 20, 30 exists, by air paths around the dielectric, at least one electrode is often fully enclosed in an insulating material, and, the exposed electrode may be grounded. The insulating material may be the same material as used for the dielectric 40, 60; however, the two materials may have differing properties. For example, the dielectric plate may be quartz and the insulating material may be a moldable material.

SUMMARY

A system for treating an object is disclosed, including an apparatus configured to create an atmospheric non-equilibrium plasma (ANEP) using a working gas in a closed storage volume sized and dimensioned to contain an object to be treated. The voltage gradient applied to the working gas may be greater than about 1.4 times an ionization voltage gradient of the working gas.

In an aspect the ANEP column length is greater than about 2.0 cm. In another aspect, the voltage applied to electrodes of the apparatus may be greater than about 50 kV RMS.

The working gas may be selected from air, O2, N2, CO2, He, Ar, or a combination of these gasses, depending on the specific object to be treated. The object may be disposed either inside or outside the ANEP column.

This technology generates reactive gas species in a sealed package. If the package is designed from a low permeability film then minutes to hours of contact time between the generated reactive gas species and the object can be realized, resulting in very large reductions in pathological microbial-species. The technique may also be used to treat objects where the desired effect is a reaction of the ionized species with surface contaminants or with the surface.

Many common packaging materials, used as the package, work well with this technology including: LDPE, HDPE, PP, PET, cardboard, Kraft paper, TYVEK (high density polyethylene fibers) and glass.

A method of treating an object is disclosed including the steps of: providing a dielectric barrier discharge (DBD) device; providing a package suitable for substantially completely enclosing the object; inserting the object into the package; filling the package with a working gas at substantially atmospheric pressure; disposing a portion of the package with respect to the DBD device such that reactive species are produced in the package by the DBD apparatus; and, activating the DBD device for a first period of time by applying a voltage gradient.

The voltage gradient applied to the DBD device is greater than approximately 1.4 times an ionization voltage gradient of the working gas. In an aspect first period of time may be less than about 15 seconds. In another aspect, the first period of time may be less than about 60 seconds. The object may be retained in the treatment volume for a second period of time so as to permit the generated reactive species to interact with the object being treated.

In an aspect the container may be manipulated so as to provide more even application of the reactive species to the object being treated.

BRIEF DESCRIPTION OF THE DRAWINGS

FIG. 2 shows (A) a portion of a DBD apparatus where a container having an object to be treated disposed between the plates of the apparatus; (B), a portion of a DBD apparatus where a container having an object to be treated is disposed between the plates of the apparatus, such that the object to be treated is not disposed between the plates of the apparatus; and, (C) a top view of a portion of the apparatus of FIG. 2A;

DESCRIPTION

Figure 1A:
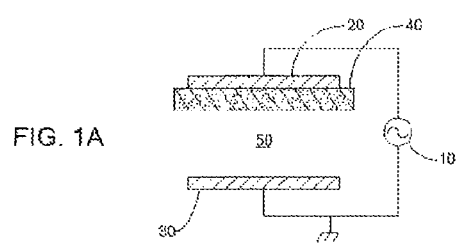
FIG. 1 (prior art) shows (A) a DBD apparatus having a single dielectric barrier; (B) a DBD apparatus having two dielectric barriers and an auxiliary capacitor for measuring the DBD charge; and, (C) a DBD apparatus with the dielectric disposed between two conducting plates.
Figure 1B:
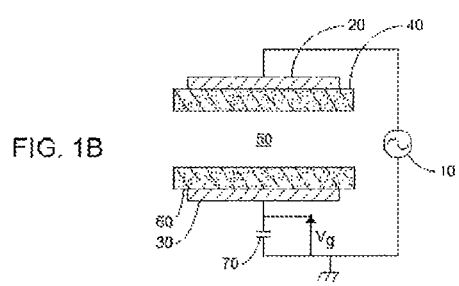
Figure 1C:
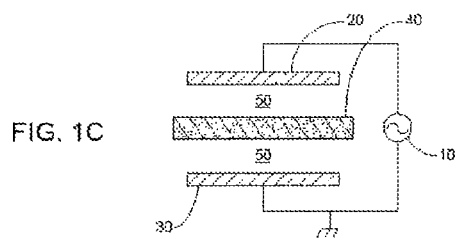

Exemplary embodiments may be better understood with reference to the drawings. Like numbered elements in the same or different drawings perform equivalent functions.

In the interest of clarity, not all the routine features of the examples herein are described. It will of course be appreciated that in the development of any such actual implementation, numerous implementation-specific decisions must be made to achieve a developer's specific goals, such as consideration of system, regulatory and business related constraints. These goals will vary from one implementation to another.

Atmospheric pressure "cold" plasmas have been shown to be effective in reducing or eliminating surface bacterial contamination of food samples. The term "cold plasma" is meant to describe a plasma discharge, which may be a non-equilibrium plasma, occurring at a pressure of about one-atmosphere and at near ambient temperature (ANEP). This is to distinguish the ANEP plasma from a thermal plasma discharge operating at a bulk gas temperature of hundreds or thousands of degrees above the ambient temperature. In a "cold plasma" at atmospheric pressure the electrons may have a significantly higher temperature than the ion and neutral species; however, the bulk temperature of the working gas is not significantly increased with respect to the ambient temperature In this context, the term "cold" should not be interpreted to require refrigeration or other cooling to perform the decontamination or treatment functions described herein; however, this does not exclude the treating or the subsequent storage of the treated object at an appropriate temperature, which may include refrigeration or cooling. Keeping the gas at a near-ambient temperature may contribute to avoidance of heat damage to the object being treated.

One technique of creating an atmospheric non-equilibrium plasma is to apply a high voltage to the volume to be ionized, while inhibiting the transition from a glow discharge to an arc discharge by limiting the discharge current. This may be done, for example, by covering at least one of the electrodes of the apparatus with a dielectric layer; resistive layers have also been used. The discharge current is self-limited by charge build up on the dielectric surface. Typically, the excitation voltage frequency is in the kHz range, but may range from power line frequencies to radio frequencies. The experimental data presented herein used a 60 Hz frequency due to the availability of high voltage transformers, whose output voltage could be easily be adjusted by controlling the input voltage thereof with a variable voltage transformer.

Dielectric-barrier discharges (DBD) are a type of alternating-current high-voltage gaseous discharges that may be formed in a nominally atmospheric pressure environment. The presence of a dielectric layer between the electrodes prevents the charge generated in the gas by the discharge from reaching at least one of the conducting electrode surfaces. Often the dielectric layer is applied to both of the electrodes. Within each half-cycle of the driving voltage waveform, when the voltage gradient applied across the gas exceeds that required for breakdown, the formation of narrow ionized discharge filaments initiates the conduction of electrons toward the more positive electrode, and ions towards the more negative electrode, although the mobility of the electrons is greater than that of the ions. An electrical charge accumulates on the dielectric layer(s) at the end(s) of each ionized filament; and, the voltage drop across the ionized filament reduces until the voltage falls below the discharge-sustaining level, so that the discharge is extinguished. The duration of the filamentary discharge is believed to be quite short: of the order of 100 nanoseconds or less. However, the resultant reactive species may have a significantly longer lifetime. The low charge mobility along the surface of the dielectric also limits the lateral region over which the gap voltage is diminished, so that a plurality of filaments may form in close proximity to one another.

Production of ozone and other reactive species in a DBD occurs between the two electrodes when operated at a particular voltage, frequency, and geometry. In air, mixtures of $O_2$ and $N_2$, or $O_2$ alone, reactive oxygen species are generated which react with each other as well as oxygen molecules resulting in the formation of ozone. Other reactive species are created when $N_2$, or other gases such as $CO_2$, $H_2O$ or Cl are present. The most oxidative species in air and oxygen gas include ozone ($O_3$), singlet oxygen (O or $O^-$), superoxide ($O_2^-$), peroxide ($O_2^{-2}$ or $H_2O_2$), and hydroxyl radicals (OH). Most of these species have very short half-lives (in the range of milliseconds); however, ozone has a much longer half-life ranging from minutes to days depending on conditions. The effects of gaseous ozone on foods has previously been studied with promising results and ozone has been shown to be more efficient at lower concentrations and treatment times than more standard sanitizers, including chlorine. Presently, the use of ozone has been limited to the treatment of unpackaged products.

The effectiveness of the system and method described herein is due to an extent on the ability to generate reactive gas species in a sealed package. If the package is fabricated from a low permeability film, then minutes to hours of contact time between the reactive gas species and the bacteria can be realized, resulting in very large reductions in microbial populations. Over the duration of the storage time, the ozone and nitrogen oxides in the package will convert back to simple oxygen and nitrogen molecules, and upon reaching a final destination (e.g., grocery store or medical supply store), the reactive gas species in the package will have been converted back to original gas composition (air or modified atmosphere).

In particular, the object to be treated may be enclosed in a sealed or substantially sealed container. The container need not be hermetic unless the level of decontamination desired is such that subsequent contamination from another source is to be avoided. Low permeability containers may retain long-lived reactive species, which may extend the effective treatment time and improve the resultant decontamination results. Non-hermetic containers may be used in applications where subsequent re-contamination of the sample is prevented by the characteristics of the packaging. Non-hermetic containers may be permeable to some extent to air, and to the other constituent gases or the radicals or reactive species produced by the ANEP. That is, the packaging may be porous to gases, but prevent spoilage or pathogenic material from entering the package. The composition of the container may be a plastic such as TYGON, low-density polyethylene (LDPE), high density polyethylene (HDP), polypropylene (PP), polyethylene terapthalate (PET), TYVEK, or polystyrene; however, various other substantially dielectric materials can be used, including, glass, wax, cardboard, paper, foil, eggshells, low dielectric constant materials, or the like. The foil may be a plastic having a thin metallic coating. This may permit the treatment of objects stored in a foil package, or having a foil liner.

An apparatus for treating a sample is shown in FIG. 2. An object to be treated 200 is placed in a substantially closed dielectric container or package 100. The container may be rigid or flexible and may be sealed by a ZIPLOC closure, by heat, by a close-fitting cap, or any other mechanism that has a similar effect. The container should have an ability to substantially retain the reactive species that are the residual of the generated ANEP plasma for a period of time that is sufficient for a particular treatment process. The working gas, which may be air, or a modified atmosphere packaging (MA) mixture, may be introduced into the container 100 prior to treatment. The container 100 may be purged prior to charging with the working gas so as to control the resulting gas mixture. The container may be sealed either permanently or temporarily prior to treatment.

A region within the container is selected where an ANEP may be generated. This may be a specific formed region of a semi-rigid or rigid container, or may be formed by manipulation of a flexible container where the gas pressure gives the container a deformable shape. In rigid containers, the gas pressure may be less than an atmosphere, while the gas pressure in a flexible container is an atmosphere or greater. This does not exclude situations, for example, where vacuum packing is used, and a working gas may be introduced for the purposes of treatment.

FIG. 2A illustrates a situation where the object being treated is disposed between the plates of the apparatus, while FIG. 2B illustrates the situation where the object being treated is disposed so that a small thickness of the storage bag having a gap between the opposing surfaces is disposed between the plates of the apparatus. For the situation of FIG. 2B, the ANEP is created inside a portion of the storage container; however, the object to be treated may not be directly exposed to the active ANEP ("out-of-field" configuration). Rather, the residual reactive species may be diffused or circulated within the volume of container having the object to be treated. This configuration may reduce the voltage needed to establish the ANEP as the distance between the electrodes may be reduced compared with the thickness of the object. In addition, where the termination of the plasma filaments on the object itself may be undesirable, that situation is avoided.

In contrast, the arrangement of FIG. 2A disposes the object to be treated between the electrodes, and the object itself may behave as a dielectric, similar to that used on one or more of the electrodes. In this circumstance, the filaments creating the ANEP may extend from the electrode, or the dielectric barrier on an electrode, or an electrode without a dielectric barrier, to a surface of the object to be treated; and an active ANEP may also surround the object ("in-field" configuration). The electrons and the ions created in the ANEP may directly impinge on the surface of the object. Similarly to the arrangement of FIG. 2B, the object may continue to be exposed to the ANEP byproducts after the active phase of ANEP generation has been completed. Each of the processes may be repeated, if needed, where the object or the storage bag or container is manipulated to better distribute the active byproducts or expose other portions of the object to the plasma or the ANEP products. Conductive objects may also be treated.

As shown in FIG. 2A, the container 100 having a working gas 300 and an object to be treated 200 may be disposed between the plates of a DBD apparatus 2. The plates 20, 30 are spaced apart so as to admit at least portion of the container 100 containing the object to be treated 200. The distance between the plates may be controlled by mechanical means, if desired, so that the container 100 may conveniently be placed between the plates 20, 30, and the spacing between the plates subsequently adjusted so as to partially compress the container 100, so as to achieve an appropriate gap spacing for the creation of the ANEP within the container 100. In this configuration, filamentary discharges may occur between the dielectric surface 40 of the top plate 20 and the opposing surface of the object 200 being treated, and may also occur between the bottom plate 30 and the object being treated 200. The ANEP may also be created by electrical currents flowing directly from one plate to another, as mediated by the dielectric layer on the plate. Other mechanical arrangements may also be used.

Where the object to be treated has the general characteristics of a dielectric material, the filaments will exhibit a behavior similar to that which would occur in a DBD apparatus without an introduced object, except that the filaments may terminate one end thereof on the object. So, the object will be directly exposed to the filamentary discharges creating the ANEP, as well as to the shorter lasting and longer lasting reactive species that are generated during the active treatment phase. As the surface density of filaments is governed by the electrical field distribution, and the shape and electrical properties of the object to be treated, the entire surface of the object may not be subject to the same intensity of direct treatment. Should more uniform treatment be desired, the object to be treated 200 may be manipulated to expose other parts of the object to direct treatment.

The high voltage is often sinusoidal and may be produced by a high-voltage transformer connected to the power grid, a signal generator connected to an amplifier, or the like. Other voltage waveform shapes may be used, including sawtooth, trapezoidal, pulsed, symmetrical, asymmetrical, or displaced from DC. The amplitude of the voltage may be controlled during operation of the apparatus by, for example, a VARIAC transformer, or by controlling the signal generator amplitude output, or the amplifier gain. The frequency of operation may be fixed or variable. In the experiments described herein, the local power line frequency (60 Hz) was used for convenience in configuring the experimental apparatus and cost considerations. ANEP plasmas can also be created using DC where a resistive layer is used as a a current limiter or ballast.

The voltage gradient at which a glow discharge is formed is a function of the constitutive gases present between the electrodes, various geometrical considerations, and the gas pressure. The constituent gases may be modified so as to achieve a desired concentration and species of ionized particles. In addition to air, $O_2$, $N_2$, $CO_2$, $H_2O$, Cl, and other mixtures, or pure gases, including inert and noble gases, are usable, depending on the application.

As shown in FIG. 2B when a flexible container 100, which may be a plastic storage bag, is used, the gas fill level may selected so a that a portion of the container may be compressed between the plates 20, 30 so as to form a smaller gap to facilitate creation of the ANEP at a lower voltage. Here, the container is shown in a state where a portion 110 of the container 100 is positioned between the electrodes of the DBD apparatus 3, so that a portion of the container 100 may be temporarily formed into a region where the ANEP may be created. The filaments creating the ANEP are formed between the surface of the dielectric 40 and the other electrode plate 30, such that the object 200 to be treated is not disposed therebetween. Portions of the container surface disposed so as to form the region in which the ANEP is to be formed may be held against the dielectric 40 and the plate 30 by the internal gas pressure. The effect of the dielectric layer of the container surface may be small, as the charge distributions are likely to be dominated by those of the electrodes and the dielectric 40.

FIG. 2C shows a top view of the DBD apparatus 3 of FIG. 2B. The dielectric material extends so as to inhibit stray discharges, and, the electrodes may be disposed opposite only a portion of the storage volume.

The electrodes may be planar, as shown; however, other geometries may be used to conform to a container such as a box, pill bottle, jar, or other shape. Shaped electrodes may be used to encourage the formation of a plasma jet, or better distribute the reaction products using induced convection. For example, large cardboard containers may be processed by using a pair of electrodes oriented at a 90° angle and placed along one or more of the edges. Similar configuration may be used for large packages of other materials and shapes.

The term package has been used to represent the enclosure, bag, container, treatment volume or storage volume in which the object is treated and subsequently stored. At least parts of the package are fabricated from a dielectric material compatible with the treatment process, and could be, for example, a bottle, a vial, an opaque plastic food tray sealed with a thin transparent film, or the like. The objects to be processed need not be dielectric, as metallic objects could be exposed as well. The apparatus and technique described herein may be used to sterilize or otherwise decontaminate objects such as medical supplies, including surgical instruments, syringes, consumer products, or other treatable objects and materials. They do not need to be removed from the packaging after treatment and until immediately prior to use. One may repeat the sterilization process in the hospital or physician's office or at a point of sale or distribution prior to opening the packaging for further suppression of contaminants or pathogens. It should be noted that the dielectric characteristics of the material forming the container may be used as the dielectric barrier of the DBD, providing that the electrical characteristics thereof prevent dielectric breakdown.

The inventors have discovered unexpected results where process or apparatus parameters such as relative humidity, voltage gradient, electrode geometry, and voltage, in addition to the gas composition and package type, may have a significant effect on performance in a sterilization or decontamination application.

The data presented herein illustrates the use of an apparatus and method of killing *Bacillus subtilis* spores, as a representative of biological contaminants, under a variety of plasma generation voltages (~13 kV, 50 kV, 80 kV RMS), electric field gradients (12.5-20 kV/cm), gap distances (1.0, 2.5 and 4.5 cm) and gas compositions (air, MA) where the object to be treated is disposed within a sealed package and either inside and outside of the plasma field. Unexpected improvements in performance obtain when certain process parameters are adjusted.

An apparatus (PK-1), is based on a dielectric barrier discharge (DBD) process, with plate electrodes comprised of insulated conductors connected to a power unit with specifications of 18 kV RMS (max) @ 30 mA @ 60 Hz. The sample package is in disposed such that opposing sides thereof are in contact with the insulated high voltage electrodes, providing a dielectric barrier between the electrodes, thereby limiting current flow through the sample package and controlling the power requirements for treatment. Only 40-50 W of power was needed to ionize an air atmosphere inside a 4 L (nominal) re-sealable plastic (LDPE) bag. Other means of insulating the electrodes, which may be a flat plate, flat wound coil, or the like, include a dielectric sheet disposed between an electrode and the package, or a dielectric layer formed around the electrode.

The high-voltage applied to the electrodes may ionize a gas, which may be a mixture of gasses, within the electric field inside the package containing the sample. The sample may be, for example, a food or a medical device. or other object to be sterilized, decontaminated or otherwise plasma treated. Ionization produced by the DBD process can result in the production of significant concentrations of reactive molecules, including ozone concentrations above 1% in a few minutes, without a noticeable increase in the sample surface temperature. Specific treatment times for targeted spore or bacterial reductions are dependent on sample contamination, packaging material, gas composition, and package/electrode configuration. The in-package ionization process has been demonstrated in a number common packaging materials including, cardboard, glass, various plastics such as LDPE, HDPE, PET, polystyrene, TYGON, rubber and others.

A second similar apparatus (PK-2) was also built and has specifications of 130 kV RMS (max) at 20 mA @ 60 Hz, so as to enable exploration of different parameters. The PK-2 system can ionize a sealed package of air with an electrode gap of up to about 10 cm.

The PK-1 and PK-2 systems were comparatively evaluated for reduction in pathological organisms by studying the reduction of *Bacillus subtilis* spores in packages containing either air or a variety of MA (modified atmosphere) gases, where the sample was disposed either inside or outside of a plasma field.

A 2×3×1×1×2×3 experimental series design was selected that utilized two voltage conditions: 13.5 kV RMS/44 W/1.0 cm gap (PK-1 ionization system) and 80 kV RMS/150 W/4.5 cm gap (PK-2 ionization system); 3 treatment conditions: infield ionization, out-of-field ionization, and no ionization; a treatment time of 300 s (PK-1) and 120 s (PK-2), respectively; room temperature; two package gas types: air (78% $N_2$, 22% $O_2$) and modified atmosphere, MA (65% $O_2$, 30% $CO_2$, 5% $N_2$); and replicated in triplicate.

Air (78% $N_2$, 22% $O_2$) and modified atmosphere (MA) gas (65% $O_2$, 30% $CO_2$, 5% $N_2$) were purchased from a local gas supplier at specified concentrations with a certificate of analysis. These gas composition(s) were then metered into sealed package at a rate of 2.1 L/min. using a shielded flow meter with stainless steel ball (Gilmont Instruments, Inc., Barrington, Ill., USA) yielding final fill volume of 1.5 L with average fill time of 45 s.

Clear, 3.78 L Ziploc™ (SC Johnson and Son, Inc., Racine, Wis., USA) heavy-duty freezer bags were obtained from a local grocery store. The bags were made of low-density polyethylene (LDPE) and had a 1.6 mm thick wall.

*Bacillus subtilis* var. *niger* (*B. atrophaeus*) spore strips (NAMSA, Northwood, Ohio, USA) with size of 3.2 cm×0.6 cm, each containing *Bacillus* populations of $1.5$-$2.5 \times 10^6$/strip or $6.18$-$6.40$ $\log_{10}$ were loaded into an open sterile petri dish inside the treatment package and then used in the experiments. For in-field ionization with PK-1 system, one end of each spore strip was secured with transparent tape to the inside of the storage bag within electrode gap space prior to treatment.

The PK-1 system was operated 13.5 kV RMS at 44 W and 60 Hz generating a 13.5 kV RMS/cm gradient between the electrodes (1.0 cm gap). The electrodes consisted of coils of wire wound around a flat dielectric object with a treatment area of 51 cm² (8.5 cm×6 cm). The PK-2 system was operated at 80 kV RMS at 150 W and 60 Hz across circular stainless steel electrodes (15 cm dia, 4.5 cm gap, 17.8 kV RMS/cm voltage gradient). The high voltage transformer of the PK-2 was obtained from Phenix Technologies, Accident, Md.

The storage bags containing spore samples were filled with the working gas (air or MA) and purged three times to ensure purity of the gas in the bag. A small, uniform amount of gas was expelled from the bag to allow for orientation of plasma electrodes if needed to achieve desired gap distance. The electrodes opposed each other, with the bag disposed therebetween and having an approximate gap distance of 1.0 cm (PK-1) and 4.5 cm (PK-2). Each system was activated for treatment times of 300 s (PK-1) or 120 s (PK-2). The gas volume in the bag was agitated manually (by pressing lightly back-and-forth on the bag) once treatment was complete to allow for a more uniform distribution of gas inside the bag prior to double-bagging for 24 h storage at room temperature (22° C.).

The temperature of the electrodes and treated storage bags was measured prior to and immediately after treatment using an infrared thermometer (Omega Engineering, Inc., Stamford, Conn., USA). All storage bag temperatures of treated samples registered at room temperature after treatment for both systems. Ozone and nitric oxide concentrations were measured immediately following the 300 s or 120 s treatments as well as after 24 h storage using DRAEGER Short-Term Detector tubes (Draeger Safety AG & Co., Luebeck, Germany) Carbon monoxide concentrations were also measured after the 24 h storage period. The tubes were chosen for ease of use with the given experimental setup and for their rapid measurement capabilities. The tubes contain a reagent which changes color upon coming into contact with the specified gas and are calibrated for specific sampling volumes. Tubes were connected to a bellows hand pump, Accuro Gas Detector Pump (Draeger Safety AG & Co., Luebeck, Germany), and calibrated such that one pump action equals 100 mL of gas. The Ozone tubes (part no. CH21001) had an indicated range of 20-300 ppm. Nitrous oxides (part no. 24001) tubes had an indicated range between 20-500 ppm. A cross-sensitivity of 50 ppm NOx per 1,000 ppm ozone was identified. Carbon monoxide tubes (part no. 33051) had an indicated range between 25-300 ppm.

It was noted that carbon monoxide tubes had an interference with ozone. Thus, no carbon monoxide measurements could be taken with ozone present. In order to determine ozone values when measuring very high concentrations, smaller gas sample volumes were collected in 5 mL or 20 mL syringes. The syringe was connected to the detection tube by means of flexible tubing. A syringe volume was expelled into the detection tube and then removed allowing total flow volume of 100 ml to occur. The observed gas concentration was then multiplied by the volume ratio of the detection tube volume over the syringe volume. The DRAEGER portable gas detection system had a precision of ±15% (Draeger Safety AG & Co., Luebeck, Germany).

Spore recoveries and aseptic methods were in accordance with manufacturer (NAMSA, Northwood, Ohio, USA) instructions for population verification of *Bacillus subtilis* spore strips. After ionization treatment and 24 h storage, each strip was aseptically removed from bag and transferred into sterile 20×150 mm test tube containing 10 mL of 0.1% sterile peptone. Seven to ten sterile 6 mm glass beads were then added to each test tube. Each test tube was vortexed (model vortexer 59, Denville Scientific, Inc., Metuchen, N.J., USA) on high speed for 120 s or until the spore strip was fully macerated into loose fibers. Test tubes were then heat shocked by placing into a 500 mL beaker with 300 mL of water heated to 90° C. and maintained at 80-85° C. for 10 minutes. Test tubes were transferred to a cold tap water bath momentarily (2 min), and then to ice water bath to rapidly cool test tubes to 0-4° C. Test tubes were then removed from ice bath and further serial dilutions were performed including $10^{-2}$, $10^{-3}$, $10^{-4}$, and/or $10^{-5}$ based on treatments or recoveries of positive (+) controls (Bacillus populations of $1.5$-$2.5 \times 10^6$/strip, $6.18$-$6.40$ $\log_{10}$). The required aliquot volumes from corresponding serial dilutions were then plated into respective petri dishes (100×15 mm) containing sterile Tryptic Soy Agar (TSA) prepared per Difco Manual specifications for spore colony enumeration [5]. TSA plates were incubated at 30-31° C. and colony growth and recoveries were monitored at 24 h, 48 h, and 72 h.

Relative humidity and temperatures inside the storage bags were measured using a Springfield® Precise Temp™ relative humidity sensor (Taylor Precision Products, Oak Brook, Ill., USA) recorded at 0 h and 24 h storage.

Figure 3:
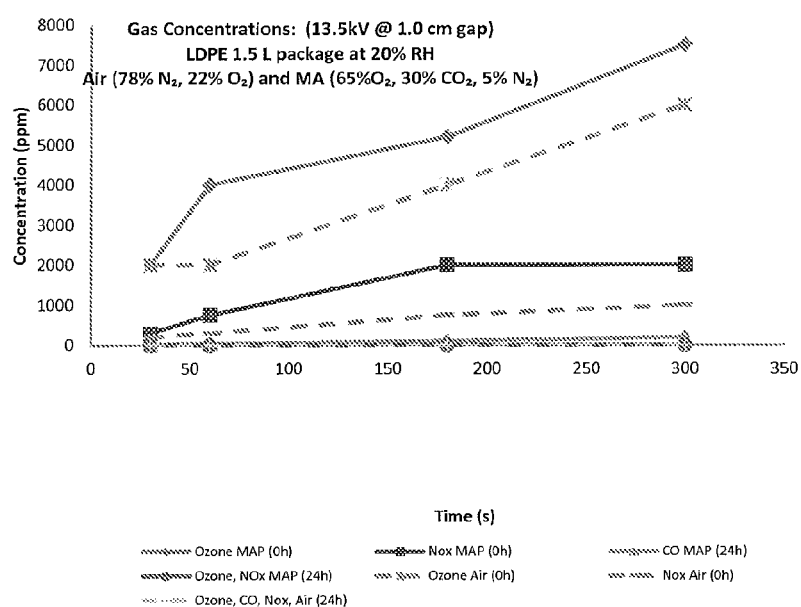
FIG. 3 shows data for gas concentrations generated using the PK-1 DBD Ionization System (13.5 kV RMS)
Figure 4:
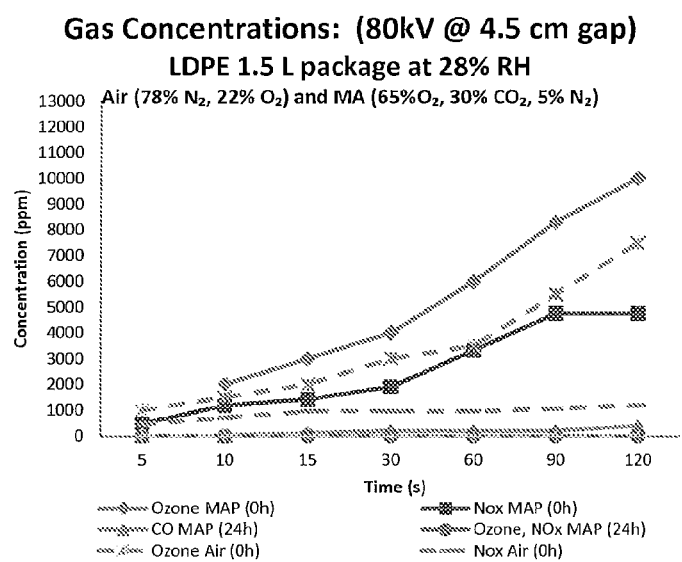
FIG. 4 shows data for gas concentrations generated using PK-2 DBD Ionization System (80 kV RMS)

FIG. 3 and FIG. 4 document the reactive oxygen species generation during in-package ionization at the specified times for both 13.5 kV and 80 kV. It can be seen from these data that high levels of reactive oxygen species can be generated for both air and MA gas. At 13.5 kV, an ozone generation rate of 1,200 and 1,500 ppm per minute were observed for air and MA gas, respectively. At 80 kV, an ozone generation rate of 3,750 ppm and 6,250 ppm per minute were observed for air and MA gas, respectively. These results suggest that increased ionization voltage increases the generation rate of reactive oxygen species. In air, the nitrous gas concentrations did not significantly change with ionization voltage. Both voltages (13.5 kV and 80 kV) achieved maximum nitrous gas concentration of approximately 1,000 ppm with an air atmosphere. However, the MA gas nitrous gas concentrations reached a significantly higher level with increased ionization voltage. Nitrous gas concentrations at 80 kV reached over 4,000 ppm at 120 seconds treatment time.

At least some of the increase in the ozone generation rate, and the resultant concentrations at the higher voltages may be attributed to the longer ionization path resulting from the 4.5 cm electrode spacing when using 80 kV in some of the experiments. However, some of the increase may also be due to the higher voltage gradients, which may also generate other reactive species that have not yet been measured. Each of the constituent gases has a different ionization potential at atmospheric pressure. These factors interact, and thus a different set of experiments would be performed to optimize these parameters.

Both ozone and nitrous oxides levels decayed to zero within 24 hours of treatment. However, there was a measurable carbon monoxide concentration in MA gas at 24-hours post-treatment with levels 200 ppm and 400 ppm for the 13.5 kV and 80 kV at treatment times of 300 s and 120 s, respectively. The current carbon monoxide measurement method did not allow measurement in the presence of ozone (e.g., time zero).

Figure 5:
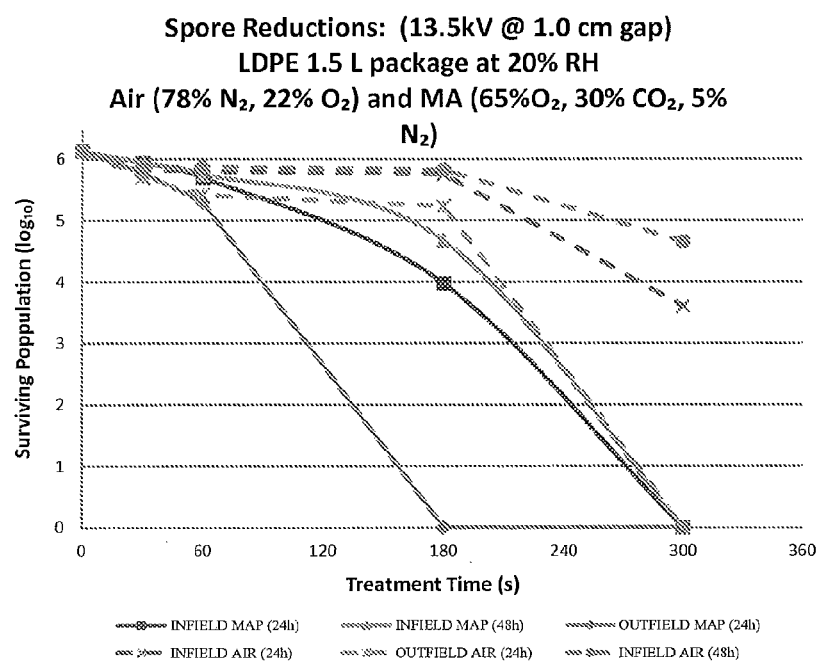
FIG. 5 shows data for spore reductions resulting from treatment by the using PK-1 DBD Ionization System (13.5 kV RMS)
Figure 6:
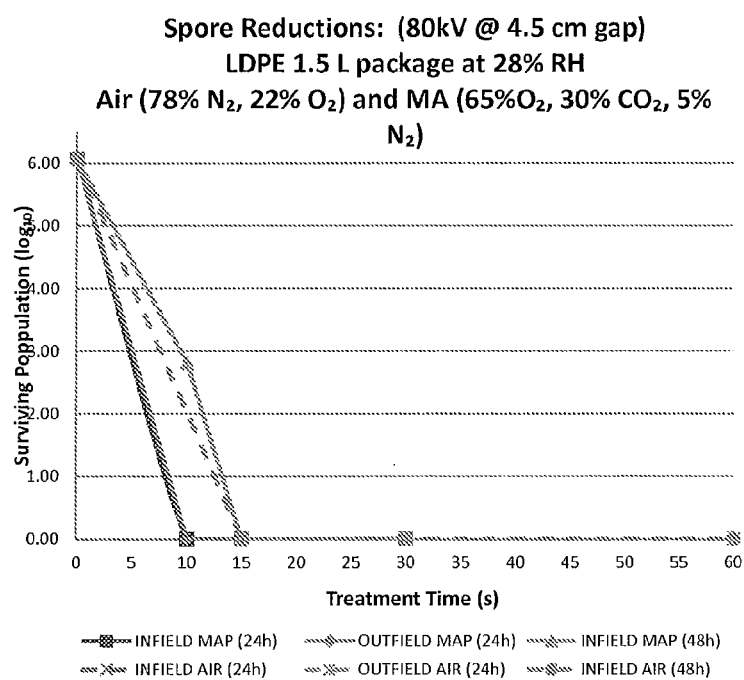
FIG. 6 shows data for spore reductions generated using PK-2 DBD Ionization System (80 kV RMS).

FIG. 5 and FIG. 6 illustrate the spore reductions achieved with ANEP treatment. In-package ionization both inside and outside of the ionization field at 13.5 kV and 80 kV may eliminate *Bacillus subtilis* spores. At 13.5 kV, treatment times for MA gas spore elimination were 180 s and 300 s for outside and inside field positioning, respectively. At 13.5 kV, treatment times for air atmosphere, spore elimination occurred at 300 s inside ionization field with insignificant spore reductions (<1.2 log) outside of the ionization field.

However, at 80 kV, complete elimination of spores was obtained in 15 s or less with no measurable difference in spore reduction rates between air and MA gas. When the samples were disposed inside the field, high voltage treatment times showed increased spore populations (>2 log) recoveries at 48 h compared to 24 h; however, no addition organisms were recovered at 72 h. These results demonstrate that using an 80 kV in-package ionization process, air or MA gas can provide complete elimination of *Bacillus subtilis* spores in 15 s or less. For these studies, dry air was used and all samples were maintained at between 20% and 30% relative humidity at room temperature. Elevated humidity may provide an even greater spore reduction rate.

Atmospheric or MA plasma may be advantageous to quickly remove microorganisms from surfaces. These experimental results clearly demonstrate the sterilization capability of in-package ionization for *Bacillus subtilis* spores, and would be indicative of results that should be obtained with other microorganisms. Using in-package ionization processes with higher ionization voltages, voltage gradients and MA gas resulting in shorter sterilization times. A complete elimination of spores was observed in less than 15 s or less for air and MA gas at 80 kV. In addition, at 13.5 kV spore elimination can be achieved with MA and air in 300 s or less.

In yet another aspect, to further understand the results of the voltage gradient and the different MA packaging atmospheres on the efficacy of in-package plasma-based sterilization, a further two-phase series of experiments was performed. In phase I, in-package ionization was performed on empty, sealed packages for sixteen gas blends and the concentrations of reactive gas species measured. The composition of these gas blends were selected to encompass a wide range of common gases (oxygen, nitrogen, carbon dioxide, helium, and argon) and shown in Table 1.

These data were used to identify three gas blends that yielded high concentrations of measured reactive gas species (e.g., ozone, nitric oxides, carbon monoxide) and, along with air, were then used for sporicidal treatment in phase II. The selection of the particular gas mixtures was appropriate for a survey experiment where a large range of valid data was being collected, rather than in an experiment exploring one or more of the mixtures in detail. As such, the selection of the gas mixtures, and the voltages and voltage gradients that were used should be understood as providing for comparable sporicidal treatment data between the differing parameters, rather than limiting the scope of the MA mixtures and processing parameters that may be desirable in a particular situation.

Phase I of this experiment series comprised a 16×7×2 experiment: 16 gas blends of $O_2$, $N_2$, $CO_2$, He, and Ar were configured (Table 1) and placed inside of packages sealed in a Cryovac B2630 high barrier package. The sealed packages (22 cm×30 cm) were filled with 1.76 L of the selected gas blend using a calibrated flow meter and stored at room temperature (22° C.). All of packages were treated in duplicate with the PK-2 ionization system at 50 kV RMS (65-75 W @ 0.5-0.8 mA) with a depth of 2.5 cm. Ionization electrodes consisted of rectangular wrappings of wire coils approximately 7.5 cm×11.5 cm placed directly above and below the center of the package. Underneath the package was a TYVEK layer (0.1905 mm) and a layer of red polypropylene (1.94 mm) sandwiched between the package and the bottom electrode The TYVEK layer was intended to simulate a bag that had layers of two different materials, as while TYVEK is a preferred material for use in medical instrument packaging, the material is not gas tight, so it would likely be combined with a gas tight polypropylene or other such bag as used in these experiments.

Treatment times used were: 0 s, 15 s, 30 s, 60 s, 150 s, 300 s, and 600 s. Ozone and nitrogen oxide gas measurements were taken using the DRAEGER gas analysis system immediately after treatment and at 24 h room temperature storage. Carbon monoxide measurements using the DRAEGER system cannot be taken in the presence of high ozone concentrations due to interference and were only taken after 24 h. Relative humidity and temperature were also recorded.

In summary, the results of phase I were that all of the selected gas blends could be ionized to generate bactericidal molecules (e.g., ozone, nitric oxides, and carbon monoxide). In general, a greater concentration of ozone was observed for gas blends with higher oxygen content, except when a noble gas (in these experiments, argon or helium) was added to the gas blends. When a noble gas was added to the gas blend, the minimum voltage needed for ionization was reduced; however, the benefit of adding noble gas to generate increased reactive gas species was mixed. Some gas blends showed increased ozone concentrations while others showed reduced ozone concentrations. Maximum ozone concentrations were obtained in gas blend #12-16,000 ppm at 150 s and 18,750 ppm at 600 s. Maximum nitric oxide concentrations of 4,500 ppm were also generated in gas blend #12 with a number of other gas blends (#10, #11, and #16) having maximum nitric oxide concentrations between 1,500 and 2,000 ppm. Carbon monoxide measurement is only available after 24 h due to measurement interference from high concentrations of nitric oxide and ozone. After 24 h storage, maximum carbon monoxide levels of 375 ppm were obtained from gas blend #9 at 600 s treatment.

In phase II of this experiment series a 4×5×2×2 experiment was performed. Four gas blends identified in phase I with significant concentration of reactive gas species were selected (shown in bold in Table 1). Active plasma treatment times used were: 0 s, 15 s, 30 s, 60 s, and 120 s. Single spore strips (1.5-2.5×$10^6$ cfu) of *Bacillus subtilis* var. *niger* were placed in open petri dishes at the center (direct exposure to the ionizing field) inside the sealed bag and at the right edge (indirect exposure) inside of the bag. The packages (22 cm×30 cm) were then sealed and filled with two liters of the selected gas (#7, #9, #12, #16) using a calibrated flow meter and stored at room temperature (22° C.). All packages were treated in duplicate with the PK-2 ionization system at 50 kV RMS (65-75 W @ 0.5-0.8 mA) with a depth of 2.5 cm. All treated packages were stored for 24 h and then bacterial spore recoveries were conducted using standard microbiological methods as previously described. In addition, a 72 hour recovery was also performed to ensure no regrowth.

In summary, for phase II, the results documented complete elimination of bacterial spores with all treatments for both direct and indirect exposure after 24 h storage. The time required for complete elimination (greater than 6 log reduction) varied with the gas blend. The shortest times for spore elimination were 60 s for both direct and indirect treatment in gas blend #9 and #16. The longest times were 120 s for gas blend #7 (air) and #12. Additional reductions in treatment times may likely be achieved by further adjustment of processing parameters such as increasing electric field voltages, reducing electrode gap, and electrode geometry. The results demonstrate that in-package ionization can eliminate bacterial spores, whether under direct or indirect exposure, from inside medical packages and potentially provides an alternative non-thermal sterilization method for these products.

TABLE 1

Selected gas blends used in Phase I of experiments. Gas blends used in Phase II are shown in bold.

| Gas Blend | $O_2$ | $N_2$ | $CO_2$ | Ar | He |
|---|---|---|---|---|---|
| 1 | 5% | 80% | 10% | — | 5% |
| 2 | 5% | 80% | 10% | 5% | — |
| 3 | 10% | 25% | 45% | — | 20% |
| 4 | 10% | 25% | 45% | 20% | — |
| 5 | 20% | 10% | 60% | — | 10% |
| 6 | 20% | 10% | 60% | 10% | — |
| (Air) 7 | 22% | 78% | — | — | — |
| 8 | 22% | 30% | 40% | — | 8% |
| 9 | 22% | 30% | 40% | 8% | — |
| 10 | 50% | 10% | 20% | — | 20% |
| 11 | 50% | 10% | 20% | 20% | — |
| 12 | 65% | 5% | 30% | — | — |
| 13 | 65% | 5% | 20% | — | 10% |
| 14 | 65% | 5% | 20% | 10% | — |
| 15 | 80% | 5% | 10% | — | 5% |
| 16 | 80% | 5% | 10% | 5% | — |

The protocol for this second series of experiments was similar to that of the first set of experiments and only salient differences in the protocol are presented.

Gas tanks with 16 different compositions were purchased from a local gas supplier at specified concentrations, each with a certificate of analysis. These gas composition(s) were then metered into sealed package at a rate of 2.112 L/min using a flow meter (Model 2260, Gilmont Instruments, Inc., Barrington, Ill., USA) yielding final fill volume of 1.76 L with average fill time of 50 s. The gas compositions were verified using an oxygen analyzer to verify oxygen concentrations.

Treatments were carried out utilizing PK-2 system. The electrodes were made from coils of wire wound around a planar dielectric form with a treatment area of 86.25 cm² (7.5 cm×11.5 cm), and spaced apart by the treatment distance: in this case 2.5 cm or 4.5 cm. The storage bags containing spore samples were filled with the working gas and purged three times to ensure purity of the gas in the bag.

The temperature of the electrodes was measured prior to and immediately after treatment using an infrared thermometer (Omega Engineering, Inc., Stamford, Conn., USA). The electrodes were allowed to cool to reach room temperature (23-25° C.) between treatments for uniform treatment temperature conditions. Relative humidity and temperatures inside the storage bags were measured using a Springfield® Precise Temp™ relative humidity sensor (Taylor Precision Products, Oak Brook, Ill., USA) recorded at 0 h and 24 h storage. Relative humidity varied daily and ranged from 20-50% for all samples tested. Ozone and nitric oxide concentrations were measured immediately following the treatment and after 24 h storage using the techniques previously described.

*Bacillus subtilis* var. *niger* (*B. atrophaeus*) spore strips (NAMSA, Northwood, Ohio, USA) with size of 3.2 cm×0.6 cm, each containing *Bacillus* populations of $1.5\text{-}2.5\times10^6$ colony forming units per strip were loaded into open sterile petri dish inside treatment package and then used in ionization treatments. Spore recoveries and aseptic methods were followed per manufacturer (NAMSA, Northwood, Ohio, USA) for population verification of *Bacillus subtilis* spore strips as previously described Gas concentrations and *Bacillus subtilis* populations were analyzed in SAS Version 9.2 (Statistical Analysis Software, Cary, N.C.). Mean comparisons were performed using the GLM Procedure and the Tukey Multiple Mean Comparison with a p<0.05.

All of 16 gas blends could be ionized to generate measurable levels of ozone, nitric oxides, and carbon monoxide under the specified conditions, with the results shown in Table 2. In general, greater concentrations of ozone were observed for gas blends with higher oxygen content except when Ar or He gas were added into gas blends. These noble gases have low ionization energy requirements, and, when blended with other gasses reduce the minimum ionization voltage gradient required. When a noble gas was blended into 22% oxygen gas blends the maximum ozone concentration increased. This is shown in the results where gas blends #8 and #9 (8% noble gas) achieved 1125 ppm ozone at 15 s ionization whereas gas #7 (air—a similar (22%) oxygen composition without noble gas) took approximately 30 s. Further, gas #7 reached a maximum ozone concentration of 2,750 ppm whereas gas mixtures #8 and #9 reached a maximum 8,000 ppm.

TABLE 2

Concentration of ozone immediately after treatment for specified gas blends. Results are color coded for noble gas additions (He addition in bold and Ar addition in italic).

| | Treatment Time | | | | | | |
|---|---|---|---|---|---|---|---|
| Gas | 0 s | 15 s | 30 s | 60 s | 150 s | 300 s | 600 s |
| #1 | 0 | *406.25* | *562.5* | *625* | *625* | *1125* | *312.5* |
| #2 | 0 | 468.75 | 1375 | 1875 | 2000 | 2000 | 750 |
| #3 | 0 | *275* | *625* | *1000* | *1500* | *2000* | *1500* |
| #4 | 0 | 375 | 1125 | 1500 | 2875 | 2750 | 1500 |
| #5 | 0 | *875* | *1625* | *2000* | *4250* | *6250* | *3750* |
| #6 | 0 | 500 | 1500 | 2125 | 4000 | 6125 | 4000 |
| #7 (Air) | 0 | 350 | 1500 | 2000 | 2750 | 2750 | 2750 |
| #8 | 0 | 1125 | 1500 | 3000 | 5000 | 10000 | 8125 |
| #9 | 0 | *1125* | *1875* | *3000* | *4750* | *11250* | *7875* |
| #10 | 0 | 2500 | 2000 | 5000 | 6250 | 7500 | 10000 |
| #11 | 0 | *2500* | *3000* | *4000* | *6125* | *9375* | *12500* |
| #12 | 0 | 2625 | 3250 | 4375 | 15000 | 16875 | 18750 |
| #13 | 0 | *625* | *1500* | *2000* | *2750* | *3000* | *4000* |
| #14 | 0 | 375 | 625 | 3000 | 2750 | 3000 | 5500 |
| #15 | 0 | *1125* | *2375* | *3375* | *5000* | *10625* | *13125* |
| #16 | 0 | *1375* | *2750* | *3750* | *4625* | *10000* | *14375* |

Interestingly, for all gas blends evaluated the maximum ozone concentration was achieved for gas blend #12 (65% $O_2$-5% $N_2$-30% $CO_2$) which contained no noble gas. It achieved ozone concentrations of 15,000 ppm at 150 s and a maximum 18,750 ppm at 600 s. This concentration of 15,000 ppm at 150 s is 2.5 times greater than any other gas blend. When noble gas was blended into a 65% $O_2$ gas (#13 and #14) reduced ozone concentrations were obtained. It is suspected that the helium ions are preferentially ionized creating lower energy electrons which in turn create less ozone and nitric oxides. Further, in gases #15 and #16 when the oxygen content is increased (80% $O_2$) and noble gas is added the ozone concentration again increases to very high levels (>10,000 ppm). The details of the plasma dynamics are not yet fully understood. However, it is clear that a range of gas and voltage parameters has been identified where efficacious results are obtained.

Nitric oxide concentrations immediately after treatment are shown in Table 3. The maximum nitric oxide concentration of 4,250 ppm were generated in gas blend #12 at 600 s with a number of other gas blends (#9, #11, and #16) having maximum nitric oxide concentrations between 1,500 and 2,000 ppm. There were no measurable concentrations of ozone or nitric oxide after 24 h. Carbon monoxide measurements were only available after 24 h due to measurement interference from high concentrations of $NO_x$ and $O_3$. After 24 h storage, maximum carbon monoxide measurements of 375 ppm CO were obtained from gas blend #9 at 600 s treatment (Table 4).

TABLE 3

Concentration of nitric oxides immediately after treatment for specified gas blends. Results are coded for noble gas additions (He addition in bold and Ar addition in italic).

| | Treatment Time | | | | | |
|---|---|---|---|---|---|---|
| Gas | 0 s | 15 s | 30 s | 60 s | 150 s | 300 s | 600 s |
| #1 | 0 | *3.5* | *6.25* | *11.25* | *18.75* | *25* | *12.5* |
| #2 | 0 | 12.5 | 56.25 | 81.25 | 100 | 131.25 | 21.25 |
| #3 | 0 | *12.5* | *18.75* | *225* | *200* | *200* | *100* |
| #4 | 0 | 7.5 | 22.5 | 87.5 | 112.5 | 100 | 50 |
| #5 | 0 | *22.5* | *37.5* | *75* | *250* | *550* | *425* |
| #6 | 0 | 16.25 | 25 | 225 | 300 | 550 | 400 |
| #7 (Air) | 0 | 31.5 | 31.5 | 75 | 450 | 900 | 700 |
| #8 | 0 | 87.5 | 112.5 | 325 | 450 | 1000 | 625 |
| #9 | 0 | 50 | 93.75 | 350 | 550 | 1500 | 875 |
| #10 | 0 | *37.5* | *137.5* | *500* | *1000* | *800* | *2000* |
| #11 | 0 | 100 | 75 | 200 | 225 | 1550 | 1750 |
| #12 | 0 | 160 | 270 | 300 | 2500 | 4250 | 4250 |
| #13 | 0 | *31.25* | *31.25* | *50* | *350* | *350* | *550* |
| #14 | 0 | 7.5 | 37.5 | 50 | 175 | 250 | 450 |
| #15 | 0 | 37.5 | 100 | 325 | 400 | 450 | 1000 |
| #16 | 0 | *43.75* | *250* | *375* | *650* | *1000* | *1560* |

TABLE 4

Concentration of carbon monoxide 24 hours after treatment for selected gas blends.

| | Treatment Time | | | | | |
|---|---|---|---|---|---|---|
| Gas | 0 s | 15 s | 30 s | 60 s | 150 s | 300 s | 600 s |
| #7 (Air) | 0 | 0 | 0 | 0 | 0 | 0 | 15 |
| #9 | 0 | 31.25 | 50 | 112.5 | 150 | 325 | 375 |
| #12 | 0 | 20 | 50 | 67.5 | 150 | 205 | 250 |
| #16 | 0 | 3 | 12.5 | 18.75 | 40 | 100 | 137.5 |

Results in phase II showed complete elimination of bacterial spores with all treatment parameters for both direct and indirect exposure of the sample and are presented in Table 5. The time required for complete elimination of the spores (greater than 6 log reduction) varied with the gas blend. The shortest times for spore elimination were 60 s for both direct and indirect treatment in gas blend #9 and #16. The longest times were 120 s for gas blend #7 (air) and #12.

TABLE 5

Spore reductions for *Bacillus subtilis* var. *niger* after treatment and 24 h storage in sealed packages of selected gas blends. 'D' indicates direct field exposure and 'I' indicates indirect field exposure. ($\log_{10}$)

| | | Treatment Time | | | | |
|---|---|---|---|---|---|---|
| Gas | D/I | 0 s | 15 s | 30 s | 60 s | 120 s |
| #7 (Air) | D | 0 | 0.398 | 0.408 | 2.39 | 6.17* |
| #7 (Air) | I | 0 | 0.419 | 0.300 | 2.63 | 6.17* |
| #9 | D | 0 | 0.365 | 3.11 | 6.40* | 6.40* |
| #9 | I | 0 | 0.450 | 3.81 | 6.40* | 6.40* |
| #12 | D | 0 | 0.345 | 0.645 | 2.80 | 6.26* |
| #12 | I | 0 | 0.310 | 0.653 | 6.26* | 6.26* |
| #16 | D | 0 | 0.513 | 2.81 | 6.39* | 6.39* |
| #16 | I | 0 | 0.592 | 2.90 | 6.39* | 6.39* |

*indicates no recoverable organisms found after 72 hrs recovery.

Additional reductions in treatment times may likely be achieved by further adjustment of processing parameters such as electric field voltages, electrode gap, and electrode geometry. The results from the studies demonstrate that with in-package ionization treatment, whether under direct or indirect exposure, bacterial spores can be eliminated from inside packages, potentially providing non-thermal sterilization for medical products.

Since the voltage gradient of about 12.5 kV/cm represents the about lowest value of ionization potential for other than the noble gasses, this value represents about a lower bound on the voltage gradient that could be effective. However, the relatively low rate of production of reactive species at the low voltage is reflected in the longer ANEP generation time to achieve an effective sporicidal effect. As many production processes place an emphasis on throughput, the reduction in processing times that can be achieved with higher voltages and voltage gradients may be beneficial. The type of MA to be selected may depend on the particular object to be processed; and, the sensitivity of the object to oxidation may place limits on the percentage composition of $O_2$ that is desirable. Carbon dioxide MA packaging gasses may preferentially produce CO and this reactant may be effective in processing certain food products.

The higher voltages and the longer ANEP column length between the electrodes contribute to both higher rates of generation and possibly to the generation of other reactants, whose effect may be seen in the reduction in processing times. Raising the processing voltage so that the voltage gradient is about 1.4 times the ionization potential of oxygen has been shown to be effective over a wide range of MA gas compositions. The combination of increasing the voltage gradient and the length of the ANEP plasma column with respect to the volume of the container has been shown to be efficacious.

TABLE 6

Brief Summary of Experimental Results

| Voltage (kV) | Voltage gradient (kV/cm) | ANEP Path Length (cm) | Ionization Volume (cm^3) | Total Package Volume (cm^3) | Ionization Volume Ratio (%) | Active treatment time for complete sterilization in MA (sec) |
|---|---|---|---|---|---|---|
| 12.5 | 12.5 | 1.0 | 86 | 500-3780 | 2.3-16.1 | 180 |
| 50 | 20 | 2.5 | 215 | 1760 | 12.2 | ~60 |
| 80 | 17.7 | 4.5 | 788 | 1500 | 52.5 | 15 |

While the methods disclosed herein have been described and shown with reference to particular steps performed in a particular order, it will be understood that these steps may be combined, sub-divided, or reordered to form an equivalent method without departing from the teachings of the present invention. Accordingly, unless specifically indicated herein, the order and grouping of steps is not a limitation of the present invention.

Although only a few examples of this invention have been described in detail above, those skilled in the art will readily appreciate that many modifications are possible without materially departing from the novel teachings and advantages of the invention. Accordingly, all such modifications are intended to be included within the scope of this invention as defined in the following claims.

What is claimed is:

1. A system for treating an object, comprising:
   an apparatus, configured to create an atmospheric non-equilibrium plasma (ANEP) in a gas in a storage volume sized and dimensioned to contain the object, the apparatus having:
   a pair of electrodes with a separation of greater than about 2.0 cm; and
   a voltage applied between the electrodes of greater than about 50 kV RMS.

2. The system of claim 1, wherein the voltage applied between the electrodes is less than about 80 kV RMS.

3. The system of claim 1, wherein the ANEP column length, the applied voltage, and the gas are selected so that an object is sterilized with the voltage applied for less than about 15 seconds, followed by a period of storage.

4. The system of claim 1, wherein the object to be treated is disposed so as to be within the ANEP column.

5. The system of claim 1, wherein the object to be treated is disposed so as to be outside the ANEP column.

6. The system of claim 1, wherein the storage volume is a dielectric.

7. The system of claim 6, wherein the dielectric is a flexible package.

8. The system of claim 6, wherein the dielectric comprises a plurality of dielectric layers.

9. The system of claim 8, wherein the plurality of dielectric layers include a gas tight layer and a layer formed of high-density polyethylene.

10. The system of claim 9, where a dielectric surface is disposed between each of the pair of electrodes and the portion of the storage volume in which the ANEP is created.

11. The system of claim 9, wherein the apparatus further comprises an alternating current voltage source connected to the electrodes.

12. The system of claim 9, wherein the storage volume is disposable such that the object is disposable between at least a pair of electrodes of the apparatus.

13. The system of claim 8, wherein the storage volume is disposable such that the object is disposable so that it is not between a pair of electrodes of the apparatus.

14. The system of claim 1, wherein the storage volume has sealable opening adapted to receive the object when the opening is in an open configuration.

15. The system of claim 1, wherein the storage volume is a polyethylene tray sealed with a plastic sheet.

16. The system of claim 1, wherein the working gas is air.

17. The system of claim 16, wherein the working gas further comprises a selectable amount of water vapor.

18. The system of claim 1, wherein the working gas is comprised of at least two gasses selected from air, $N_2$, $O_2$, $CO_2$, He, or Ar.

19. The system of claim 1, wherein the ANEP is generated for a period of about 15 seconds or less.

20. The system of claim 1, wherein the ANEP is generated for a period of 60 seconds or less.

21. The apparatus of claim 1, wherein the gas comprises at least 10% $O_2$.

22. The apparatus of claim 1, wherein the gas comprises at least 10 percent $CO_2$.

23. The apparatus of claim 1, wherein the gas comprises at least 10% $O_2$ and less than about 20% of a noble gas.

24. The apparatus of claim 1, wherein the gas comprises not more than 20% of a noble gas.

25. The apparatus of claim 1, wherein the gas comprises not more than 20% of a noble gas and at least 10% $CO_2$.

* * * * *